United States Patent [19]

Talebian et al.

[11] Patent Number: 4,895,936
[45] Date of Patent: Jan. 23, 1990

[54] PLATINUM PHARMACEUTICALS

[75] Inventors: Abdolhossen Talebian, Herndon; Dianna C. Green, Falls Church, both of Va.; Philip S. Schein, Bryn Mawr, Pa.

[73] Assignee: Georgetown University, Washington, D.C.

[21] Appl. No.: 143,761

[22] Filed: Jan. 14, 1988

Related U.S. Application Data

[63] Continuation-in-part of Ser. No. 74,825, Jul. 17, 1987, abandoned.

[51] Int. Cl.$^4$ .................... C07H 15/00; C07H 23/00
[52] U.S. Cl. .................................. 536/17.1; 536/121
[58] Field of Search .............................. 536/17.1, 121

[56] References Cited

U.S. PATENT DOCUMENTS 4,284,579  8/1981  Meischen .................... 260/429 R
4,551,524  11/1985  Kidani ........................ 536/121
4,575,550  3/1986  Totani ........................ 536/121

OTHER PUBLICATIONS

*Cisplatin: Current Status and New Developments*, Stephen K, Carter, Academic Press, 1980, pp. 317–431.
O. Gandolfi et al., "Aminomalonato(1,2—Diaminocyclohexane)Platinum(II)," *Inorganica Chimica Acta*, vol. 135, pp. 27–31, 1987.
M. P. Hacker et al., "Water—Soluble N—Substituted Iminodacetato(1,2—Diaminocyclohexane)—Platinum (II) Complexes as Potential Antitumor Agents," *Cancer Research*, vol. 46, pp. 6250–6254, 1986.

L. A. Zwelling, "Cisplatin and New Platinum Analogs," *Cancer Chemotherapy* 7, Ch. 8, pp. 105–122, 1985.

*Primary Examiner*—Johnnie H. Brown
*Assistant Examiner*—Pamela S. Webber
*Attorney, Agent, or Firm*—Wegner & Bretschneider

[57] ABSTRACT

Platinum compounds useful in the treatment of cancer are disclosed. Compositions containing these compounds and methods of using the same are also discussed. The compound have the formula:

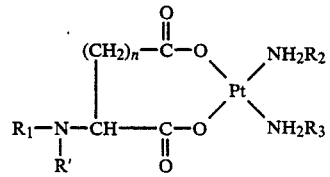

wherein n is 0 or 1, $R_1$ is selected from the group consisting of hydrogen, a mono or disaccharide or a derivative thereof linked to the nitrogen atom by a —NHCO— amide moiety, an —NHCS— thioamide moeity or a —CO— carbonylmoiety, R' is selected from the group consisting of hydrogen and $C_{1-4}$ alkyl, and $R_2$ and $R_3$ are selected from the group consisting of hydrogen, $C_{1-4}$ alkyl or $R_2$ and $R_3$ or $R_2$ and $R_3$ together are linked to adjacent carbon atoms on a four, five or six membered ring structure, or $R_2$ and $R_3$ together form a fused or bicyclic ring with adjacent carbon atoms; with the proviso that R' and $R_1$ cannot both be hydrogen when n=o, or a pharmaceutically acceptable salt thereof.

13 Claims, No Drawings

PLATINUM PHARMACEUTICALS

This application is a continuation-in-part of Ser. No. 074,825, filed July 17, 1987, now abandoned.

BACKGROUND OF THE INVENTION

Platinum anti-cancer agents are known in the literature. One of the most well publicized of the platinum anti-cancer agents is cis-diammine-dichloroplatinum (II), also known as cis-DDP and cisplatin. A discussion of cisplatin and its usefulness in the treatment of various types of cancer, such as testicular carcinoma, bladder cancer, ovarian cancer, and head and neck cancer can be found in Zewlling, *Cancer Chemotherapy*, pp. 105–122 (1985).

Problems arise when such platinum agents are used in cancer treatment however. The toxicity of platinum to the bone marrow and kidneys precludes large sized dosages which can, in effect, render such treatment ineffective. Also, the overall desirability of and confidence in chemotherapy based upon known platinum active ingredients is decreased due to the drastic consequences to bone marrow and kidneys of the use of toxic levels of platinum.

SUMMARY OF THE INVENTION

The present invention is directed toward platinum anti-cancer agents having increased water solubility. Such an increase in water solubility aids the body in passing the platinum out of the system, thus preserving healthy bone marrow and kidneys. The water solubility of the platinum anti-cancer agents is enhanced by the presence of a mono or disaccharide group on the platinum active ingredient compound.

Pharmaceutical compositions containing the active ingredient and methods of treating carcinoma by administering said compositions to patients suffering from carcinoma are also discussed.

DETAILED DESCRIPTION OF THE INVENTION

In a first aspect of the present invention, there is provided a compound of the formula:

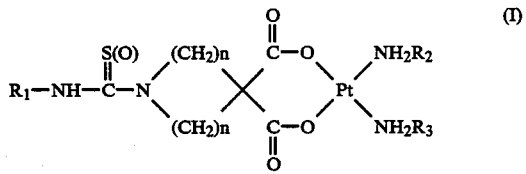

wherein n is 1 or 2; $R_1$ is a mono or disaccharide or derivative thereof; each of $R_2$ and $R_3$ is independently selected from the group consisting of hydrogen or $C_{1-4}$ alkyl, or $R_2$ and $R_3$ together are linked to adjacent carbon atoms on a five or six membered ring structure or a pharmaceutically acceptable salt thereof.

The symbol "(O)" next to the sulfur atom indicates that an oxygen atom may replace the sulfur atom in the structure of the present invention.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the first aspect of the present invention involves a compound of the formula (I), wherein $R_1$ is a mono or disaccharide or derivative thereof selected from the group consisting of glucose, galactose, mannose, glucosamine and galactosamine and derivatives thereof.

Another preferred embodiment of the first aspect of the present invention involves a compound of formula (I), wherein $R_2$ and $R_3$ are hydrogen.

Still another preferred embodiment of the first aspect of the present invention involves a compound of formula (I), wherein $R_2$ and $R_3$ together are linked to adjacent carbon atoms on a five or six membered ring structure.

Another preferred embodiment of the first aspect of the present invention involves a compound of the formula:

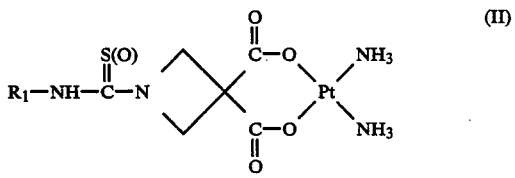

and $R_1$ is selected from the group comprising glucose, mannose, galactose, glucosamine, galactosamine and derivatives thereof.

Further preferred in a first aspect of the present invention is a compound, wherein the compound is of the formula:

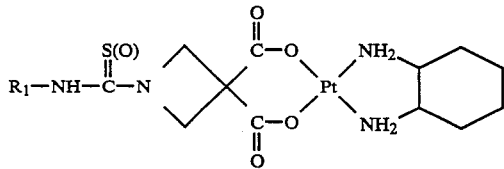

and $R_1$ is selected from the group comprising glucose, mannose, galactose, glucosamine, galactosamine and derivatives thereof.

Additionally preferred in the first aspect of the present invention is a compound, wherein the compound is of the formula:

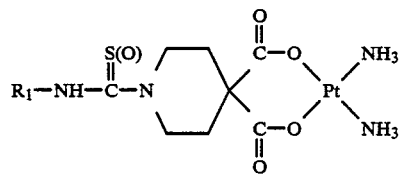

and $R_1$ is selected from the group comprising glucose, mannose, galactose, glucosamine, galactosamine and derivatives thereof.

Another preferred embodiment of the first aspect of the invention is a compound, wherein the compound is of the formula:

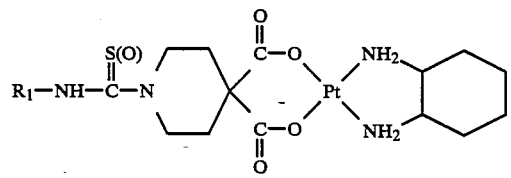

and $R_1$ is selected from the group comprising glucose, mannose, galactose, glucosamine, galactosamine and derivatives thereof.

A second aspect of the present invention involves a compound of the formula:

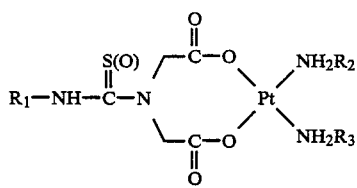

wherein $R_1$ is a mono or disaccharide or a derivative thereof, $R_2$ and $R_3$ are selected from the group consisting of hydrogen, $C_{1-4}$ alkyl or $R_2$ and $R_3$ or $R_2$ and $R_3$ together are linked to adjacent carbon atoms on a five or six membered ring structure
or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the second aspect of the present invention involves a compound of the formula (VI), wherein $R_1$ is a mono or disaccharide or derivative thereof selected from the group consisting of glucose, galactose, mannose, glucosamine and galactosamine and derivatives thereof.

Another preferred embodiment of the second aspect of the present invention involves a compound of formula (VI), wherein $R_2$ and $R_3$ are hydrogen.

Still another preferred embodiment of the second aspect of the present invention involves a compound of formula (VI), wherein $R_2$ and $R_3$ together are linked to adjacent carbon atoms on a five or six membered ring structure.

Further preferred in the second embodiment is a compound, wherein the compound is of the formula:

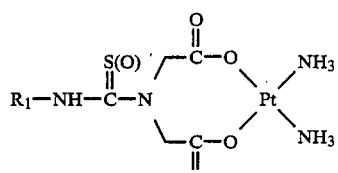

and $R_1$ is selected from the group comprising glucose, mannose, galactose, glucosamine, galactosamine and derivatives thereof.

Additionally preferred in the second embodiment is a compound, wherein the compound is of the formula:

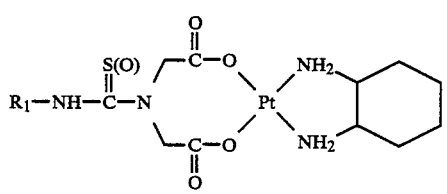

and $R_1$ is selected from the group comprising glucose, mannose, galactose, glucosamine, galactosamine and derivatives thereof.

Also preferred within the second aspect of the present invention is a compound of the formula:

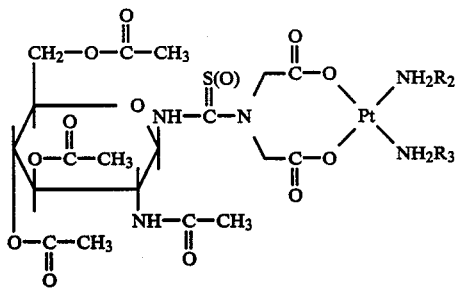

wherein $R_2$ and $R_3$ are as defined above.

In a third aspect of the present invention, there is provided a compound of the formula:

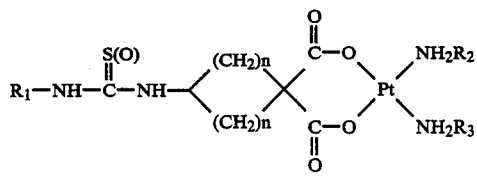

wherein n is 1 or 2; $R_1$ is a mono or disaccharide or derivative thereof; each of $R_2$ and $R_3$ is independently selected from the group consisting of hydrogen or $C_{1-4}$ alkyl, or $R_2$ and $R_3$ together are linked to adjacent carbon atoms on a five or six membered ring structure or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of this aspect involves a compound, wherein said compound is of the formula:

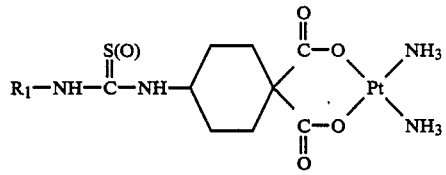

and $R_1$ is selected from the group comprising glucose, mannose, galactose, glucosamine, galactosamine and derivatives thereof.

An additional preferred embodiment of the present invention involves a compound, wherein said compound is of the formula:

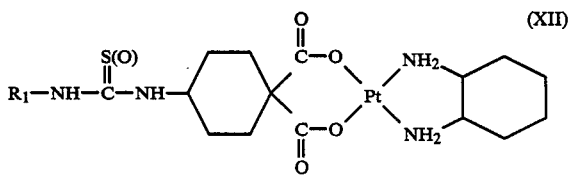

and $R_1$ is selected from the group comprising glucose, mannose, galactose, glucosamine, galactosamine and derivatives thereof.

In a fourth aspect of the present invention, there is provided a compound of the formula

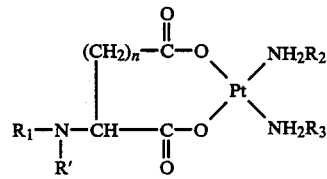

wherein n is 0 or 1, $R_1$ is selected from the group consisting of hydrogen, a mono or disaccharide or a derivative thereof linked to the nitrogen atom by a —NH—CO— amide moiety, an —NHCS— thioamide moiety, or a —CO— carbonyl moiety, R' is selected from the group consisting of hydrogen and $C_{1-4}$ alkyl, and $R_2$ and $R_3$ are selected from the group consisting of hydrogen, $C_{1-4}$ alkyl or $R_2$ and $R_3$ or $R_2$ and $R_3$ together are linked to adjacent carbon atoms on a four, five or six membered ring structure, or $R_2$ and $R_3$ together form a fused or bicyclic ring with adjacent carbon atoms; with the proviso that R' and $R_1$ cannot both be hydrogen when n=0, or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a fused or polycyclic ring there are contemplated rings of the following formulae:

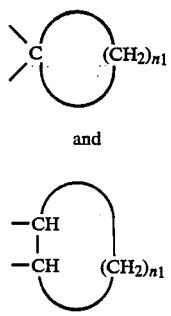

wherein $n_1$ is selected from 1, 2, 3, 4, 5 or 6.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the third aspect of the present invention involves a compound of the formula (X), wherein $R_1$ is a mono or disaccharide or derivative thereof selected from the group consisting of glucose, galactose, mannose, glucosamine and galactosamine and derivatives thereof.

Another preferred embodiment of this aspect of the present invention involves a compound of formula (X), wherein $R_2$ and $R_3$ are hydrogen.

Still another preferred embodiment of the fourth aspect of the present invention involves a compound of formula (X), wherein $R_2$ and $R_3$ together are linked to adjacent carbon atoms on a five or six membered ring structure.

Further preferred in this aspect is a compound, wherein the compound is of the formula:

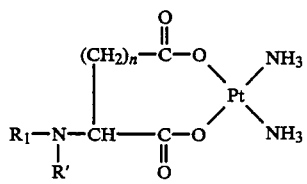

(XIV)

Also embodied in this aspect of the present invention is a compound, wherein the compound is of the formula:

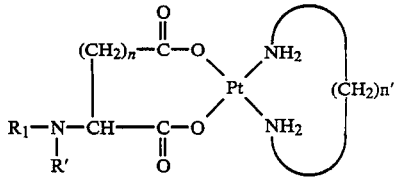

(XV)

wherein n' is 1, 2 or 3.

Another embodiment of this aspect of the present invention contemplates a compound, wherein $R_2$ and $R_3$ together form a fused or bicyclic ring with adjacent carbon atoms.

A preferred embodiment of the present invention involves a compound, wherein said compound is (L-aspartato-O,O')-(1,2-cyclohexanediammine-N,N')-platinum (II).

An additional embodiment involves a compound, wherein said compound is diammine-2-[[[[3,4,6-tri-O-acetyl-2-(N-acetylamino)-2-deoxy-alpha-D-glucopyranosyl]amino]thioxomethyl]amino]butanedioato-O,O']-platinum (II).

A further embodiment of the present invention involves a compound, wherein said compound is 2-[[[[3,4,6-tri-O-acetyl-2-(N-acetylamino)-2-deoxy-alpha-D-glucopyranosyl]amino]thioxomethyl]amino]-butanedioato-O,O']-(1,2-cyclohexanediammine-N,N')-platinum (II).

In accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (I) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anti-cancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution An isotonic solution of the invention may contain in addition to said compound, water and salt, also conventional ingredients such as glucose.

A preferred composition of the present invention involves a composition, wherein said compound, i.e. active ingredient, is of formula (I) and is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (I), and is such that $R_2$ and $R_3$ are hydrogen.

Still another preferred composition of the present invention involves a composition, wherein said compound is of formula (I) and is such that $R_2$ and $R_3$ together are linked to adjacent carbon atoms on a five or six membered ring structure.

Additional preferred compositions of the present invention involve compositions, wherein the active compound therein is a compound of formulae (II), (III), (IV) and (V).

Also, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (VI) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anti-cancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention involves a composition, wherein said compound, i.e. active ingredient, and is of formula (VI) is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (VI) and is such that $R_2$ and $R_3$ are hydrogen.

Still another preferred composition the present invention involves a composition, wherein said compound is of formula (VI) and is such that $R_2$ and $R_3$ together are linked to adjacent carbon atoms on a five or six membered ring structure.

Additional preferred compositions of the present invention involve compositions, wherein the active compound therein is a compound of formulae (VII), (VIII) and (IX).

Also, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (X) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anti-cancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

Preferred compositions of the present invention involve compositions, wherein the active compound therein is a compound of formulae (XI) and (XII).

Moreover, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (XIII) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anti-cancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention involves a composition, wherein said compound, i.e. active ingredient, and is of formula (XIII) is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (XIII) and is such that $R_2$ and $R_3$ are hydrogen.

Still another preferred composition the present invention involves a composition, wherein said compound is of formula (XIII) and is such that $R_2$ and $R_3$ together are linked to adjacent carbon atoms on a five or six membered ring structure.

Additional preferred compositions of the present invention involve compositions, wherein the active compound therein is a compound of formulae (XIV) and (XV), (L-aspartato-O,O')-(1,2-cyclohexanediammine)-N,N'-platinum (II), diammine-2-[[[[3,4,6-tri-O-acetyl-2-(N-acetylamino)-2-deoxy-alpha-D-glucopyranosyl]amino]thioxomethyl]amino]butanedioato-O,O']-platinum (II), and 2-[[[[3,4,6-tri-O-acetyl-2-(N-acetylamino)-2-deoxy-alpha-D-glucopyranosyl]amino]thioxomethyl]amino]butanedioato-O,O']-(1,2-cyclohexanediammine-N,N')-platinum (II).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (I) and a pharmaceutically acceptable carrier therefor to a patient suffering from said ailments.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient. A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

A preferred method of the present invention involves the administration of a compound of formula (I), wherein said compound is such that $R_1$ is a mono or disaccharide or derivative thereof selected from the group consisting of glucose, galactose, mannose, glucosamine and galactosamine and derivatives thereof.

Another preferred method of the present invention involves the administration of a compound of formula (I), wherein said compound is such that $R_2$ and $R_3$ are hydrogen.

A further method of the present invention involves the administration of a compound of formula (I), wherein said compound is such that $R_2$ and $R_3$ together are linked to adjacent carbon atoms on a five or six membered ring structure.

Additional preferred methods of the present invention involve the administration of a compound, wherein the compound therein is a compound of formulae (II), (III), (IV), and (V).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (VI) and a pharmaceutically acceptable carrier therefor to a patient suffering from said ailment.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient. A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

A preferred method of the present invention involves the administration of a compound of formula (VI), wherein said compound is such that $R_1$ is a mono or disaccharide or derivative thereof selected from the group consisting of glucose, galactose, mannose, glucosamine and galactosamine and derivatives thereof.

Another preferred method of the present invention involves the administration of a compound of formula (VI), wherein said compound is such that $R_2$ and $R_3$ are hydrogen.

A further method of the present invention involves the administration of a compound of formula (VI), wherein said compound is such that $R_2$ and $R_3$ together are linked to adjacent carbon atoms on a five or six membered ring structure.

Additional preferred methods of the present invention involve administration of compounds, wherein the compound therein is a compound of formulae (VII), (VIII) and (IX).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (X) and a pharmaceutically acceptable carrier therefor to a patient suffering from said ailment.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient. A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

Additional preferred methods of the present invention involve administration of compounds, wherein the compound therein is a compound of formulae (XI) and (XII).

Still further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (XIII) and a pharmaceutically acceptable carrier therefor to a patient suffering from said ailments.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient. A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

A preferred method of the present invention involves the administration of a compound of formula (XIII), wherein said compound is such that $R_1$ is a mono or disaccharide or derivative thereof selected from the group consisting of glucose, galactose, mannose, glucosamine and galactosamine and derivatives thereof.

Another preferred method of the present invention involves the administration of a compound of formula (XIII), wherein said compound is such that $R_2$ and $R_3$ are hydrogen.

A further method of the present invention involves the administration of a compound of formula (XIII), wherein said compound is such that $R_2$ and $R_3$ together are linked to adjacent carbon atoms on a five or six membered ring structure.

Additional preferred methods of the present invention involve the administration of a compound, wherein the compound therein is a compound of formulae (XIV) and (XV), (L-aspartato-O,O')-(1,2-cyclohexanediammine)-N,N'-platinum (II), diammine-2-[[[[3,4,6-tri-O-acetyl-2-(N-acetylamino)-2-deoxy-alpha-D-glucopyranosyl]amino]thioxomethyl]amino]butanedioato-O,O']-platinum (II), and 2-[[[[3,4,6-tri-O-acetyl-2-(N-acetylamino)-2-deoxy-alpha-D-glucopyranosyl- ]amino]thioxomethyl]amino]butanedioato-O,O']-(1,2-cyclohexanediammine-N,N')-platinum (II).

The thio compounds of formula (I) of the present invention may be prepared according to the following reaction scheme:

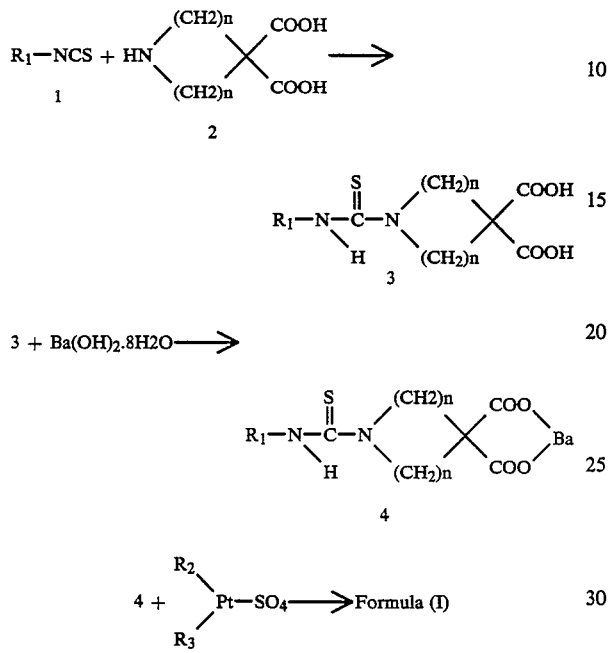

The oxo derivatives can be made in accordance with an analogous method with an $R_1$—NCO starting material.

The compound of formula (VI) may also be made in accordance with the above reaction scheme with the substitution of the following reactant 2 into the first reaction step.

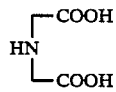

The compounds of the third aspect of the present invention can be prepared according to an analogous reaction mechanism utilizing a cycloalkyl containing starting material.

The thio compounds of formula (XIII) may be prepared in accordance with the following reaction scheme.

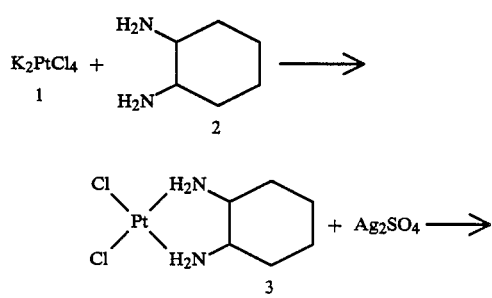

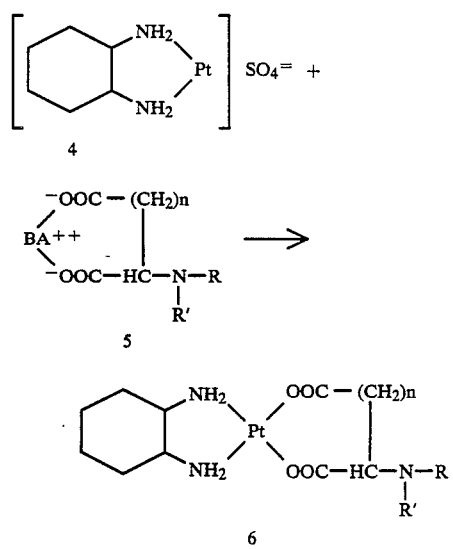

The following are exemplary of the present invention.

EXAMPLE I 1.2 g of 2-(N-acetylamino)-3,4,6-tri-O-acetyl-2-deoxyglucopyranosyl isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide .8H$_2$O. The resultant is added to 0.4 grams of cissulfato-(cyclohexane-1,2-diammine-N,N')-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt/complex of [[[2-(N-acetylamino)-3,4,6-tri-O-acetyl-2-deoxyglucopyranosyl]amino]thioxomethyl]imino-diacetic acid.

EXAMPLE II

The compound of Example I is admixed with an isotonic solution to produce a dosage form suitable for intravenous administration. 130 mg/m$^2$ body surface area of a patient is administered to said patient through intravenous administration over a period of 24 hours.

EXAMPLE III 1.2 g of tetra-O-acetyl-D-mannopyranosyl-isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography (CHCl3:methanol, 9:1) shows complete disappearance of isothiocyanate. Acetonitrile is removed under reduced pressure and the water layer is basified with saturated sodium bicarbonate and is then extracted with CHCl3. The aqueous layer is acidified with 10% HCl and is extracted with ethylacetate. The ethylacetate layer is backwashed with water and is dried over Na2SO4. The product is further dried through evaporation in vacuo. A intermediate of formula 3 is formed by recrystallization from ethylether.

0.52 g of this intermediate is admixed with 0.3 g barium hydroxide 8H2O. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammine-platinum(II) salt/complex of [[[tetra-O-acetyl-D-mannopyranosyl]amino]thioxomethyl]imino-diacetic acid.

EXAMPLE IV

The compound of Example III is admixed with an isotonic solution to produce a dosage form suitable for intramuscular administration. 80 mg/m$^2$ body surface area of a patient is administered to said patient through intramuscular administration daily.

EXAMPLE V 1.2 g of tetra-O-acetyl-D-galactopyranosyl-isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography (CHCl3:methanol, 9:1) shows complete disappearance of isothiocyanate. Acetonitrile is removed under reduced pressure and the water layer is basified with saturated sodium bicarbonate and is then extracted with CHCl3. The aqueous layer is acidified with 10% HCl and is extracted with ethylacetate. The ethylacetate layer is backwashed with water and is dried over Na2SO4. The product is further dried through evaporation in vacuo. A intermediate of formula 3 is formed by recrystallization from ethylether.

0.52 g of this intermediate is admixed with 0.3 g barium hydroxide 8H2O. The resultant is added to 0.4 grams of cissulfato cyclohexane-1,2-diammine-N,N'-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt/complex of [[[tetra-O-acetylgalactopyranosyl]amino]-thioxomethyl]imino-diacetic acid.

EXAMPLE VI

The compound of Example V is admixed with an isotonic solution to produce a dosage form suitable for intraperitoneal administration. 100 mg/m$^2$ body surface area of a patient is administered to said patient through intraperitoneal administration weekly.

EXAMPLE VII 1.2 g of 3,4,6-tri-O-acetyl-2-(N-acetylamino)-2-deoxy-alpha-D-glucopyranosyl-isothiocyanate in 5 ml acetonitrile is added to a solution of 0.413 g of iminodiacetic acid and 1.12 ml of N,N-diisoppropylethylamine in 25 ml of a water-acetonitrile mixture (1:1 V/V). The resulting mixture is stirred until thin layer chromatography (CHCl3:methanol, 9:1) shows complete disappearance of isothiocyanate. Acetonitrile is removed under reduced pressure and the water layer is basified with saturated sodium bicarbonate and is then extracted with CHCl3. The aqueous layer is acidified with 10% HCl and is extracted with ethylacetate. The ethylacetate layer is backwashed with water and is dried over Na2SO4. The product is further dried through evaporation in vacuo. A intermediate of formula 3 is formed by recrystallization from ethylether.

0.52 g of this intermediate is admixed with 0.3 g barium hydroxide.8H2O. The resultant is added to 0.4 grams of cissulfato-amino-methylamino-N,N'-platinum(II) which is already in solution with 20 ml of water. This mixture is stirred at room temperature for 2 hours. Next the barium sulfate is filtered off, and the resulting filtrate is evaporated under reduced pressure to yield a amino-methylamino-N,N'-platinum(II) salt/complex of [[[3,4,6-tri-O-acetyl-2-(N-acetylamino)-2-deoxy-alpha-D-glucopyranosyl]amino]thioxomethyl]imino diacetic acid.

EXAMPLE VIII

The compound of Example VII is admixed with an hydroxypropylcellulose to form a dosage form suitable for oral administration. 120 mg/m$^2$ body surface area of a patient is administered to said patient through oral administration daily.

EXAMPLE IX 1.2 g of 3,4,6-tri-O-acety-2-(N-acetylamino)-2-deoxy-alpha-D-galactopyranosyl-isothiocyanate in 5 ml acetonitrile is added to a solution of 0.413 g of 4-amino-1,1-cyclohexanedicarboxylic acid and 1.12 ml of diisopropylethylamine in 25 ml of a water-acetonitrile mixture (1:1 V/V). The resulting mixture is stirred until thin layer chromatography (CHCl3:methanol, 9:1) shows complete disappearance of isothiocyanate. Acetonitrile is removed under reduced pressure and the water layer is basified with saturated sodium bicarbonate and is then extracted with CHCl3. The aqueous layer is acidified with 10% HCl and is extracted with ethylacetate. The ethylacetate layer is backwashed with water and is dried over Na2SO4. The product is further dried through evaporation in vacuo. A intermediate of formula 3 is formed by recrystallization from ethylether.

0.52 g of this intermediate is admixed with 0.3 g barium hydroxide.8H2O. The resultant is added to 0.4 grams of cissulfato-cyclopentane-1,2-diammine-N,N'-platinum(II) which is already in solution with 20 ml of water. This mixture is stirred at room temperature for 2 hours. Next the barium sulfate is filtered off, and the resulting filtrate is evaporated under reduced pressure to yield a cyclopentane-1,2-diammineplatinum(II) salt/complex of 4-[[[3,4,6-tri-O-acetyl-2-(N-acetylamino)-2-deoxy-alpha-D-galactopyranosyl]amino]thioxomethyl]-1,1-cyclohexanedicarboxylic acid.

EXAMPLE X

The compound of Example IX is admixed with an isotonic solution to produce a dosage form suitable for intravenous administration. 150 mg/m$^2$ body surface area of a patient is administered to said patient through intravenous administration over a period of 24 hours.

EXAMPLE XI 1.2 g of 2-(N-acetylamino)-3,4,6-tri-O-acetyl-2-deoxyglucopyranosyl isothiocyanate in 5 ml acetonitrile is added to a solution of 0.413 g of 3,3-trimethyleneimino dicarboxylic acid and 1.12 ml of N,N-diisopropylethylamine in 25 ml of a water-acetonitrile mixture (1:1 V/V). The resulting mixture is stirred until thin layer chromatography ($CHCl_3$:methanol, 9:1) shows complete disappearance of isothiocyanate. Acetonitrile is removed under reduced pressure and the water layer is basified with saturated sodium bicarbonate and is then extracted with $CHCl_3$. The aqueous layer is acidified with 10% HCl and is extracted with ethylacetate. The ethylacetate layer is backwashed with water and is dried over $Na_2SO_4$. The product is further dried through evaporation in vacuo. A intermediate of formula 3 is formed by recrystallization from ethylether.

0.52 g of this intermediate is admixed with 0.3 g barium hydroxide.$8H_2O$. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of 2-(N-acetylamino)-3,4,6-tri-O-acetyl-2-deoxyglucopyranosyl-amino-thioxomethyl-3,3-trimethyleneimino-dicarboxylic acid.

EXAMPLE XII

The compound of Example XI is admixed with an isotonic solution to produce a dosage form suitable for intramuscular administration. 50 mg/m$^2$ body surface area of a patient is administered to said patient through intramuscular administration daily.

EXAMPLE XIII 1.2 g of tetra-O-acetyl-glucopyranosyl-isothiocyanate in 5 ml acetonitrile is added to a solution of 0.413 g of 4-amino-1,1-(cyclohexanedicarboxylic acid and 1.12 ml of N,N-diisopropylethylamine in 25 ml of a water-acetonitrile mixture (1:1 V/V). The resulting mixture is stirred until thin layer chromatography ($CHCl_3$:methanol, 9:1) shows complete disappearance of isothiocyanate. Acetonitrile is removed under reduced pressure and the water layer is basified with saturated sodium bicarbonate and is then extracted with $CHCl_3$. The aqueous layer is acidified with 10% HCl and is extracted with ethylacetate The ethylacetate layer is backwashed with water and is dried over $Na_2SO_4$. The product is further dried through evaporation in vacuo. A intermediate of formula 3 is formed by recrystallization from ethylether.

0.52 g of this intermediate is admixed with 0.3 g barium hydroxide.$8H_2O$. The resultant is added to 0.4 grams of cissulfato-(cyclohexane-1,2-diammine-N,N')-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt/complex of 4-[[(tetra-O-acetyl-alpha-D-glucopyranosyl)amino]thioxomethyl]amino]-1,1-cyclohexanedicarboxylic acid.

EXAMPLE XIV

The compound of Example XIII is admixed with an isotonic solution to produce a dosage form suitable for intraperitoneal administration. 150 mg/m$^2$ body surface area of a patient is administered to said patient through intraperitoneal administration every 3 weeks.

EXAMPLE XV 1.2 g of 2-(N-acetylamino)-3,4,6-tri-O-acetyl-2-deoxyglucopyranosyl isothiocyanate in 5 ml acetonitrile is added to a solution of 0.413 g of 3,3-trimethyleneiminodicarboxylic acid and 1.12 ml of diisopropylethylamine in 25 ml of a water-acetonitrile mixture (1:1 V/V). The resulting mixture is stirred until thin layer chromatography ($CHCl_3$:methanol, 9:1) shows complete disappearance of isothiocyanate. Acetonitrile is removed under reduced pressure and the water layer is basified with saturated sodium bicarbonate and is then extracted with $CHCl_3$. The aqueous layer is acidified with 10% HCl and is extracted with ethylacetate. The ethylacetate layer is backwashed with water and is dried over $Na_2SO_4$. The product is further dried through evaporation in vacuo. A intermediate of formula 3 is formed by recrystallization from ethylether.

0.52 g of this intermediate is admixed with 0.3 g barium hydroxide.$8H_2O$. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of 2-(N-acetylamino)-3,4,6-tri-O-acetyl-2-deoxyglucopyranosyl-amino-thioxomethyl-3,3-trimethyleneimino-dicarboxylic acid.

EXAMPLE XVI

The compound of Example XV is admixed with glycerin monostearate to produce a dosage form suitable for oral administration. 70 mg/m$^2$ body surface area of a patient is administered to said patient through oral administration daily.

EXAMPLE XVII 1.2 g of tetra-O-acetyl-galactopyranosyl-isothiocyanate in 5 ml acetonitrile is added to a solution of 0.413 g of 3,3-trimethyleneiminodicarboxylic acid and 1.12 ml of N,N-diisopropylethylamine in 25 ml of a water-acetonitrile mixture (1:1 V/V) The resulting mixture is stirred until thin layer chromatography ($CHCl_3$:methanol, 9:1) shows complete disappearance of isothiocyanate. Acetonitrile is removed under reduced pressure and the water layer is basified with saturated sodium bicarbonate and is then extracted with $CHCl_3$. The aqueous layer is acidified with 10% HCl and is extracted with ethylacetate. The ethylacetate layer is backwashed with water and is dried over $Na_2SO_4$. The product is further dried through evaporation in vacuo. A intermediate of formula 3 is formed by recrystallization from ethylether.

0.52 g of this intermediate is admixed with 0.3 g barium hydroxide.$8H_2O$. The resultant is added to 0.4 grams of cissulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of tetra-O-acetyl-galactopyranosyl-amino-thioxomethyl-3,3-trimethyleneiminodicarboxylic acid.

EXAMPLE XVIII

The compound of Example XVII is admixed with glycerin monostearate to produce a dosage form suitable for oral administration. 70 mg/m² body surface area of a patient is administered to said patient through oral administration daily.

EXAMPLE XIX 1.2 g of tetra-O-acetyl-glucopyranosyl isothiocyanate in 5 ml acetonitrile is added to a solution of 0.413 g of 4,4-piperidinedicarboxylic acid and 1.12 ml of N,N-diisopropylethylamine in 25 ml of a water-acetonitrile mixture (1:1 V/V). The resulting mixture is stirred until thin layer chromatography (CHCl₃:methanol, 9:1) shows complete disappearance of isothiocyanate. Acetonitrile is removed under reduced pressure and the water layer is basified with saturated sodium bicarbonate and is then extracted with CHCl₃. The aqueous layer is acidified with 10% HCl and is extracted with ethylacetate. The ethylacetate layer is backwashed with water and is dried over Na₂SO₄. The product is further dried through evaporation in vacuo. A intermediate of formula 3 is formed by recrystallization from ethylether.

0.52 g of this intermediate is admixed with 0.3 g barium hydroxide.8H₂O. The resultant is added to 0.4 grams of cissulfato-cyclohexane-1,2-diammine-platinum(II) which is already in solution with 20 ml of water. This mixture is stirred at room temperature for 2 hours. Next the barium sulfate is filtered off, and the resulting filtrate is evaporated under reduced pressure to yield a 1,2-cyclohexane-diammino-platinum(II) salt/complex of 4-[[[(tetra-O-acetyl-glucopyranosyl)amino]thioxomethyl]amino]-4,4-piperidinedicarboxylic acid.

EXAMPLE XX

The compound of Example XV is admixed with hydroxypropylcellulose to produce a dosage form suitable for oral administration. 100 mg/m² body surface area of a patient is administered to said patient through oral administration daily.

EXAMPLE XXI

The cyclohexane-1,2-diammine-platinum(II) salt of 2-(acetylamino)-3,4,6-tri-O-acetyl-2-deoxy-glucopyranosyl-aminothioxomethyl-imino diacetic acid and cisplatin were tested against murine P388 leukemia. The murine P388 leukemia system is known to be sensitive to cisplatin. The leukemia was maintained intraperitoneally in female DBA/2 mice.

Prior to administration, cisplatin was dissolved in ethanol. The solution was then adjusted to 5% ethanol, 95% sterile water. The cyclohexane-1,2-diammine-platinum(II) salt of 2-(acetylamino)-3,4,6-tri-O-acetyl-2-deoxyglucopyranosylaminothioxomethyl-imino diacetic acid was dissolved in sterile water at 4 degrees celsius immediately prior to administration.

Each compound was administered intraperitoneally to groups of CD2F₁ male mice on day 1 after intraperitoneal implantation of 1×10⁶ P388 leukemia cells. P388 antileukemic activity for each compound was assessed by mean survival days and percentage increased life span (% ILS).

% ILS is calculated as follows:

$$\%ILS = (T-C)/C \times 100$$

wherein T is the mean survival days of the treated mice and C is the mean survival days of the untreated mice. The results of the experimentation are shown in the following table.

TABLE 1

| Compound | Dose | % ILS | Mean Survival (days) |
|---|---|---|---|
| cisplatin | 10 mg/kg | 83 | 17.4 |
| invention | 100 mg/kg | 80 | 17.1 |

EXAMPLE XXII

Preparation of Dicarboxylic Acid Ligand 3,4,6-tri-O-acetyl-2-(acetylamino)-2-deoxy-glucopyranosyl isothiocyanate is added to a solution of aspartic acid and N,N-diisopropylethylamine in a mixture of water-acetonitrile. The mixture is stirred at room temperature in the dark until thin-layer chromatography (chloroform:methanol 10:1) indicates reaction completion. Acetonitrile is removed and the water layer is basified with 10% Na HCO₃. The basic solution is extracted with 2×75 ml CH₂Cl₂, is acidified with 10% HCl and is extracted with 2×100 ml of ethyl acetate. The ethyl acetate layer is dried over anhydrous Na₂SO₄ and is evaporated to dryness to give 2-[[[3,4,6-tri-O-acetyl-2-(N-acetylamino)-2-deoxy-alpha-D-(glucopyranosyl]amino]thioxomethyl]amino]butanedioic acid. M.p. 124–126.

EXAMPLE XXIII

Preparation of Cis-Sulfato-DACH-Platinum (II)

To a freshly prepared solution of K₂PtCl₄ is added an equimolar amount of 1,2-cyclohexanediamine in distilled water. This mixture is allowed to react at room temperature in a nitrogen atmosphere protected from light for 8 hours. The precipitate is washed successively with 10% HCl, H₂O, ethanol, acetone and ether. After drying in vacuo over P₂O₅ over night, the cis-dichloro-(1,2-cyclohexanediammine)-platinum (II) is stirred with an equimolar amount of silver sulfate in distilled, degassed water under nitrogen atmosphere for 36 hours in the dark. The silver chloride precipitate is removed and the filtrate is freeze dried to give cis-sulfato-DACH-platinum (II).

EXAMPLE XXIV

Cis-sulfato-DACH-platinum (II) is prepared in accordance with Example XXIII. Barium L-aspartate is prepared in situ using the appropriate dicarboxylic ligand. The cis-sulfato-DACH-platinum (II) and barium L-aspartate are combined and are agitated in a nitrogen atmosphere in the dark for 2 hours. Barium sulfate precipitate is filtered off and the filtrate is concentrated to about 2 ml. Acetone is added to the concentrated solution resulting in a white precipitate. This precipitate is further purified by successive washing with acetone and ether. The resulting product is (L-aspartato-O,O')-(1,2-cyclohexanediammine-N,N')-platinum (II). (Turned brown at 240, decomposed at 280).

EXAMPLE XXV 5.1 mmol Cis-Pt(NH$_3$)I$_2$ is added to 5 mmol Ag$_2$SO$_4$ in 200 ml degassed, distilled water and is stirred in the dark at room temperature for 4 hours. AgI precipitate is filtered off and the filtrate is concentrated to about 80 ml. A solution of 5 mmol barium 2-[[[3,4,6-tri-O-acetyl-2-(N-acetylamino-2-deoxy-alpha-D-glucopyranosyl-]amino]thioxomethyl]amino]butanedioate is prepared in situ using the appropriate dicarboxylic ligand which is prepared in accordance with Example XXII. The barium compound is combined with the cis-diammine-sulfato-platinum (II) solution and the mixture is agitated at room temperature for 2 hours. Barium sulfate precipitate is filtered off and the filtrate is concentrated to about 1 ml. Acetone is added to the concentrated solution resulting in a yellow precipitate. This precipitate is further purified by successive washing with acetone and ether. The resulting product is Diammine 2-[[[[3,4,6-tri-O-acetyl-2-(N-acetylamino)-2-deoxy-alpha-D-glucopyranosyl]amino]thioxomethyl]amino]butanedioate-O,O']-platinum (II). (Decomposed at 190).

EXAMPLE XXVI

Cis-sulfato-DACH-platinum (II) is prepared in accordance with Example XXIII. Barium 2-[[[3,4,6-tri-O-acetyl-2-(N-acetylamino)-2-deoxy-alpha-D-glucopyranosyl]amino]thioxomethyl]amino]butanedioate is prepared in situ using the appropriate dicarboxylic ligand which is prepared in accordance with Example XXII. The cis-sulfato-DACH-platinum (II) and barium 2-[[[3,4,6-tri-O-acetyl-2-(N-acetylamino)-2-deoxy-alpha-D-glucopyranosyl]amino]thioxomethyl]amino]-butanedioate are combined and are agitated in a nitrogen atmosphere in the dark for 2 hours. Barium sulfate precipitate is filtered off and the filtrate is concentrated to about 2 ml. Acetone is added to the concentrated solution resulting in a white precipitate. This precipitate is further purified by successive washing with acetone and ether. The resulting product is 2-[[[[3,4,6-tri-O-acetyl-2-(N-acetylamino)-2-deoxy-alpha-D-glucopyranosyl]amino]thioxomethyl]amino]butanedioate-O,O']-(1,2-cyclohexanediammine)-N,N'-platinum (II). (Turned brown at 200, decomposed at 260).

EXAMPLE XXVII

The compound 2-[[[3,4,6-tri-O-acetyl-2-(N-acetylamino)-2-deoxy-alpha-D-glucopyranosyl]amino]-thioxomethyl]amino]butanedioato-O,O']-[1,2-cyclohexanediammine-N,N']platinum (II) and cisplatin were tested against murine P388 leukemia. The murine P388 leukemia system is known to be sensitive to cisplatin. The leukemia was maintained intraperitoneally in female DBA/2 mice.

Prior to administration, cisplatin was dissolved in sterile saline (0.85% sodium chloride). The compound 2-[[[3,4,6-tri-O-acetyl-2-(N-acetylamino)-2-deoxy-alpha-D-glucopyranosyl]amino]thioxomethyl]amino]-butanedioato-O,O']-[1,2-cyclohexanediammine-N,N']platinum (II) was dissolved in sterile water at 4° C. immediately prior to administration.

Each compound was administered intraperitoneally to groups of CD2F$_1$ male mice on day 1 after intraperitoneal implantation of 1×10$^6$ P388 leukemia cells. P388 antileukemic activity for each compound was assessed by mean survival days and percentage increased life span (% ILS).

% ILS is calculated a follows:

$$\% ILS = (T-C)/C \times 100$$

wherein T is the mean survival days of the treated mice and C is the mean survival days of the untreated mice. The results of the experimentation are shown in the following table.

TABLE TABLE 2

| compound | Dose | % ILS | Mean Survival (days) |
|---|---|---|---|
| cisplatin | 10 mg/kg | 96 | 15.7 |
| invention | 400 mg/kg | 76 | 14.1 |
| invention | 800 mg/kg | toxic | — |

What is claimed is:

1. A compound of the formula:

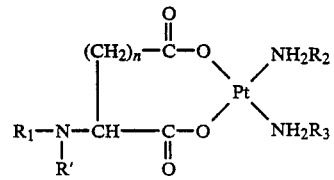

wherein n is 0 or 1; R$_1$ is selected from the group consisting of hydrogen, a mono or disaccharide which has a five or six membered ring component selected from the group consisting of pyranosyl, furanosyl, sugar alcohols, deoxysugars, glyconic acids, glycuronic acids and glycosides, which can be substituted by acetyl, amino or N-acetylamino linked to the nitrogen atom by a —NHCO— amide moiety, and —NHCS— thioamide moiety or a —CO— carbonylmoiety, R' is selected from the group consisting of hydrogen, C$_{1-4}$ alkyl or R$_2$ and R$_3$ or R$_2$ and R$_3$ together are linked to adjacent carbon atoms on a four, five or six membered ring structure, or R$_2$ and R$_3$ together form a fused or bicyclic ring with adjacent carbon atoms; with the proviso that R' and R$_1$ cannot both be hydrogen when n=0, or a pharmaceutically acceptable salt thereof.

2. A compound of claim 1, wherein R$_1$ is a mono or disaccharide or derivative thereof selected from the group consisting of glucose, galactose, mannose, glucosamine and galactosamine.

3. A compound of claim 1, wherein R$_2$ and R$_3$ are hydrogen.

4. A compound of claim 1, wherein R$_2$ and R$_3$ together are linked to adjacent carbon atoms on a four, five or six membered ring structure.

5. A compound of claim 1, wherein R$_2$ and R$_3$ together form a fused or bicyclic ring with adjacent carbon atoms.

6. A compound of claim 1, wherein R$_2$ and R$_3$ together form a group of the following formula:

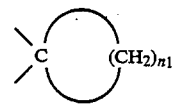

wherein n$_1$ is selected from 1, 2, 3, 4, 5 or 6.

7. A compound of claim 1, wherein R$_2$ and R$_3$ together form a group of the following formula:

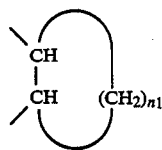

wherein $n_1$ is selected from 1, 2, 3, 4, 5 or 6.

8. A compound of claim 1, wherein said compound is of the formula

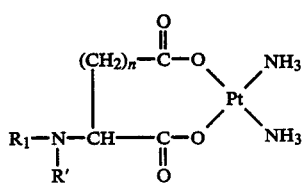

and $R^1$ and $R'$ are defined as in claim 1.

9. A compound of claim I, wherein said compound is of the formula

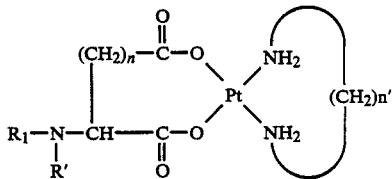

and $R_1$ and $R'$ are defined as in claim 1 and n, is 1, 2 or 3.

10. A compound of claim 1, wherein said compound is (L-aspartato-O,O')-(1,2-cyclohexanediammine-N,N')-platinum (II).

11. A compound of claim 1, wherein said compound is diammine-2-[[[[3,4,6-tri-O-acetyl-2-(N-acetylamino)-2-deoxy-alpha-D-glucopyranosyl]amino]thioxomethyl]amino]butanedioato-O,O']-platinum (II).

12. A compound of claim 1, wherein said compound is 2-[[[[3,4,6-tri-O-acetyl-2-(N-acetylamino)-2-deoxy-alpha-D-glucopyranosyl]amino]thioxomethyl]amino]-butanedioato-O,O']-(1,2-cyclohexanediammine-N,N')-platinum (II).

13. A compound as claimed in claim 1, wherein the derivative is selected from the group consisting of sugar alcohols, dioxy sugars, glyconic acids, glycuronics acids, glycocites, acetyl substituted derivatives, amino substituted derivatives and N-acetylamino substituted derivaties.

* * * * *